| United States Patent [19] | [11] Patent Number: 4,822,877 |
|---|---|
| Inada et al. | [45] Date of Patent: Apr. 18, 1989 |

[54] MODIFIED HAEM

[75] Inventors: Yuji Inada; Katsunobu Takahashi, both of Tokyo, Japan

[73] Assignees: Suntory Limited, Osaka; Bellex Corporation, Tokyo, both of Japan

[21] Appl. No.: 11,216

[22] Filed: Feb. 5, 1987

[30] Foreign Application Priority Data

Feb. 5, 1986 [JP] Japan .................................. 61-23577

[51] Int. Cl.$^4$ ............................................ C07D 487/22
[52] U.S. Cl. ..................................................... 540/145
[58] Field of Search ......................................... 540/145

[56] References Cited

FOREIGN PATENT DOCUMENTS 60-58983 4/1985 Japan .
60-58984 4/1985 Japan .
60-58985 4/1985 Japan .

Primary Examiner—Richard L. Raymond
Attorney, Agent, or Firm—Cushman, Darby & Cushman

[57] ABSTRACT

The invention provides a modified haem which is chemically coupled with a polyalkylene glycol methyl ether or an ω-amino derivative thereof through at least one of the two carboxyl groups in said haem molecule. The modified haem has a peroxidase activity and is soluble in water or various organic solvents.

3 Claims, 5 Drawing Sheets

MODIFIED HAEM

FIELD OF THE INVENTION

This invention relates to a novel modified haem which has a peroxidase activity and is soluble in various organic solvents and neutral aqueous solutions as well.

The improved solubility in water or organic solvents renders the modified haem of the invention particularly suitable for use in the detection of peroxides in samples such as blood, foods or cosmetics, since use of organic solvents is unavoidable for extracting peroxides from such samples. The haem of the invention which is soluble in organic solvents, can be added to the extracted peroxide solution in an organic solvent to quantify it by use of the enzyme action of the modified haem of the invention.

PRIOR ART

Haem represent a group of substances which naturally occur as complexes with proteins. For example, protohaem or protohaemin exist as a prosthetic group in haemoglobin or in haemin enzymes such as cytochrome C, peroxidase etc. In addition, haem itself has peroxidase activity which catalzses the following reaction:

$$2AH + H_2O \rightarrow 2A + 2H_2O$$

or $$2AH + ROOH \rightarrow 2A + ROH + H_2O$$

and for this reason it can be used in place of haemin enzymes.

However, even though it is soluble in a diluted aqueous alkaline, haem is insoluble in water in the neutral pH range wherein reactions catalyzed by haemin enzymes normally take place. In addition, it has extremely low solubility in most organic solvents (such as benzene, toluene, chloroform, alcohol, ether) to be used for quantitative determination of the peroxides in lipid fractions extracted from these organic solvents.

SUMMARY OF THE INVENTION

The present invention provides a novel haem and its salt haemin which has been so modified that it simultaneously exhibits hydrophilic and hydrophobic characteristics in order to make it soluble both in various organic solvents and in aqueous solutions at a neutral pH.

The invention further provides a chemically modified haem which is active as a peroxidase in aqueous solutions in the neutral pH range or in organic solvents.

The invention further provides a chemically modified haem which is superior to naturally occurring haemin enzymes in terms of stability, especially with respect to the effect of temperature, whereby it can be used in reactions at higher temperatures or can be stored at ambient temperature for a prolonged period without any loss of activity.

DETAILED DESCRIPTION OF THE INVENTION

The modified haem of the invention comprises a haem which is chemically coupled with a polyalkylene glycol methyl ether or an ω-amino-derivative thereof through at least one of the two carboxyl groups in said haem molecule.

Haem as used herein refers to various porphyrin-iron complexes or salts thereof with an acid in general. Salts of haem with an acid are usually called haemin. The modified haem of the invention as used herein includes salts of haem (haemin) modified in the same manner. Protohaem and protohaemin are typical examples. The modified haem of the invention may be coupled through the ester-bonding or the amido-bonding at one or both of the two carboxyl groups.

A typical form of polyalkylene glycol methyl ether or its ω-amino derivative for use in the invention is polyethylene glycol methyl ether of the formula:

$$CH_3O-(CH_2CH_2O)_n-H$$

or its ω-amino derivative which is derived from the former by substitution at its terminal hydroxyl group with amino group. In the above formula, 'n' is preferably chosen to be such a number that the molecular weight of the ether or its derivative will be between 750 and 10,000, preferably 2,000 and 5,000.

The modified haem of the invention can be prepared by a suitable conventional method for preparing esters or amides. For example, haem or haematin is reacted with a polyalkylene glycol methyl ether or its ω-amino derivative in the presence of a condensation agent such as dicyclohexylcarbodiimide and chlorocarbonic ester (ClCOOR; R=CH$_3$, C$_2$H$_5$, C$_3$H$_7$ and C$_4$H$_9$). The reaction will require 1 to 2 days at room temprature in an appropriate solvent such as pyridine trimethylamine and dimethylaniline, which is inert to the reactants. Alternatively, polyalkylene glycol monomethyl ether can be activated to form aminoethoxy polyalkyleneglycol monomethyl ether by a conventional method which is then used to react with haem to couple through an acid-amide bonding in the presence of a condensation agent as mentioned above.

The modified haem so obtained is soluble in aqueous solutions of neutral pH range, and is also soluble in aromatic hydrocarbon solvents such as benzene, toluene, etc., or in chlorinated hydrocarbon solvents such as chloroform, 1,1,1-trichloroethane, or ethereal solvents such as dioxane. The absorption spectrum of the product of the invention shows absorption bands in the Soret band which is characteristic to porphyrin compounds; namely around 396 nm in water and around 401 nm in chloroform.

The invention will be described hereunder in more detail with reference to non-limiting examples. In the examples, the subscript after "PEG" represents the number of modified carboxyl groups in the haemin;

EXAMPLE 1

Preparation of modified haemin (1) PEG-Haemin-1 (Haemin which is modified with ω-amino derivative of polyethyleneglycol monomethyl ether through an acid amide bonding)

Figure 1:
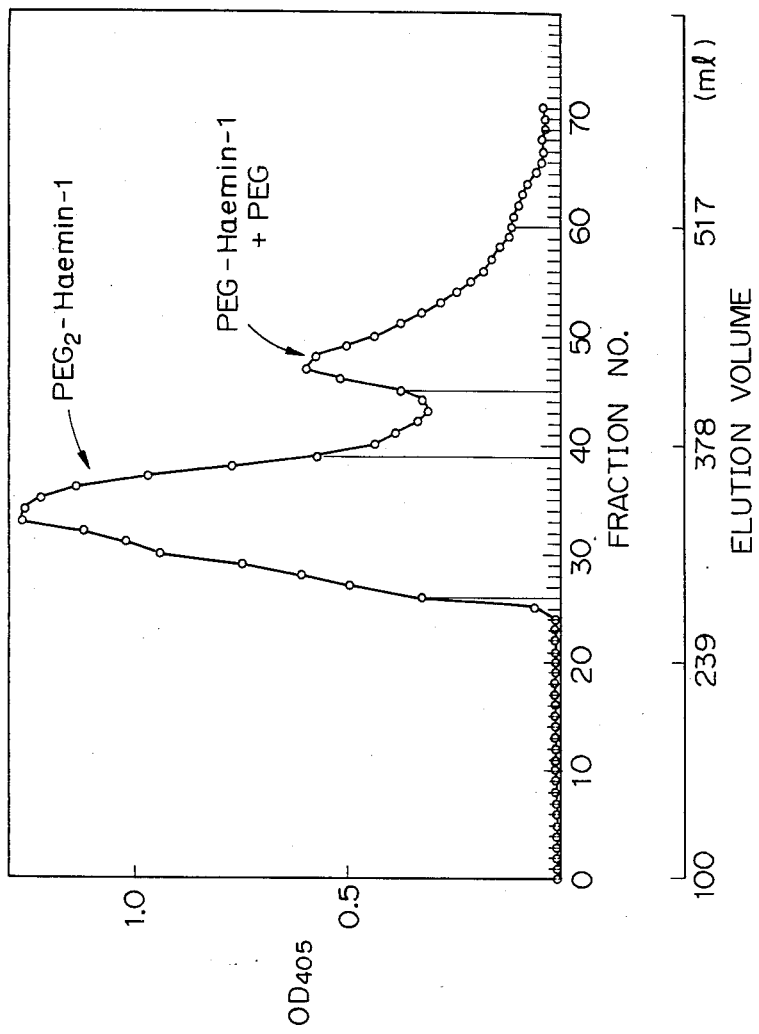
FIG. 1 shows the chromatographic pattern of PEG-haemin-1 from the gel filtration column in Example 1 (1)
Figure 2:
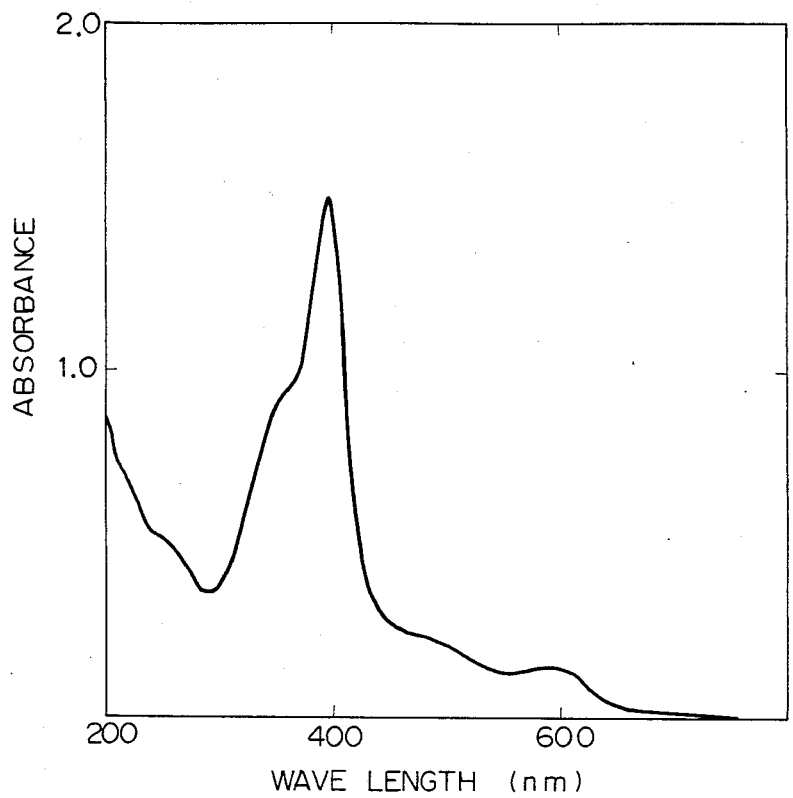
FIG. 2 shows visible to UV absorption spectrum of PEG$_2$-haemin-1 in Example 1 (1)
Figure 4:
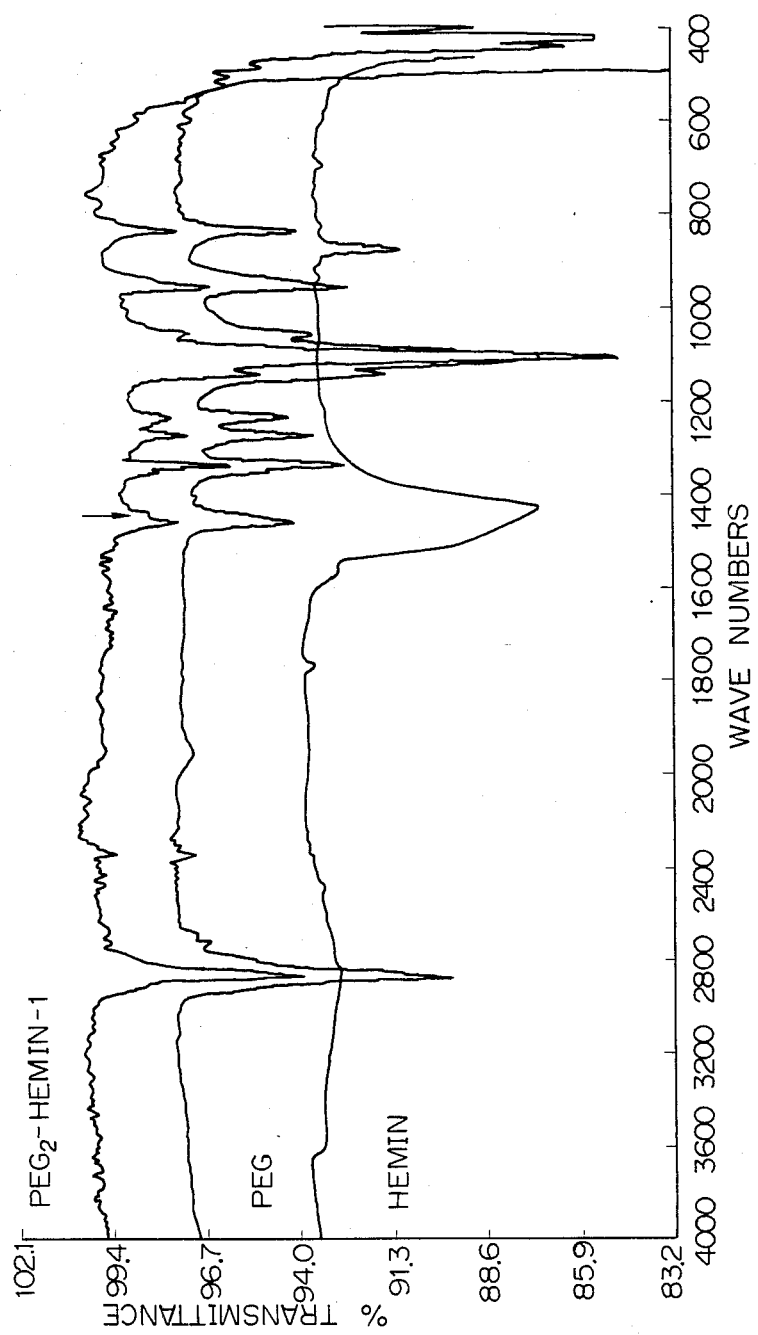
FIG. 4 shows IR spectrum of PEG$_2$-haemin-1 in Example 1 (1)

Polyethyleneglycol monomethyl ether (average molecular weight 5,000) (100 g) was tosylated by a conventional method. Potassium phthalimide was added thereto to obtain a phthalimide derivative. The product was mixed with hydrazine to remove the phthalic acid moiety whereby aminoethoxy polyethylene glycol methyl ether (PEG-NH$_2$,72.6 g) was obtained. Haemin (ferriprotoporphyrin chloride) (300 mg) and PEG-NH$_2$ (5 g) were dissolved in pyridine (50 ml), molecular sieve 3A (2.5 g) was added to adequately remove water, and a condensation agent dicyclohexylcarbodiimide (1.25 g) was then added to complete the formation of acidamide bonding whereupon the modified haemin of the invention (PEG-haemin) was obtained in a substantially quantitative yield. PEG-haemin was purified from the reaction product by introducing the latter to a gel filtration column of Sephadex LH-60. Two main peaks were eluted as shown in the chromatographic pattern in FIG. 1. The peak comprised of fraction numbers 26 to 38 had a molecular weight over 10,000. These fractions were pooled as the modified haem of which two carboxyl groups had been modified with PEG-NH$_2$. The solvent was removed by evaporation to obtain the target product (0.2733 g) which was designated as PEG$_2$-haemin-1. Fraction numbers 45 to 60 which constituted a smaller peak having a molecular weight a little higher than 5,000 comprised a mixture of unreacted PEG-NH$_2$ and the modified haem (PEG$_1$-haemin-1) having one carboxyl group modified with PEG-NH$_2$. The combined fractions 45 to 60 were treated as stated above and the modified haem having one PEG-NH$_2$ group was obtained as a mixture (0.1051 g) with unreacted PEG-NH$_2$. FIG. 2 shows the visible to UV absorption spectrum of the purified PEG$_2$-haemin-1. FIG. 4 shows the IR spectrum of PEG$_2$-haemin-1 in Example 1 (1). IR spectra of PEG and the unmodified haemin are also shown. PEG$_2$-haemin-1 gave a small shoulder on the peak near wave number 1,500 which evidences the coupling of the haemin and PEG-NH$_2$.

(2) PEG-Haemin-2 (Haemin which is modified with poplyethyleneglycol monomethyl ether through an ester bonding)

Figure 3:
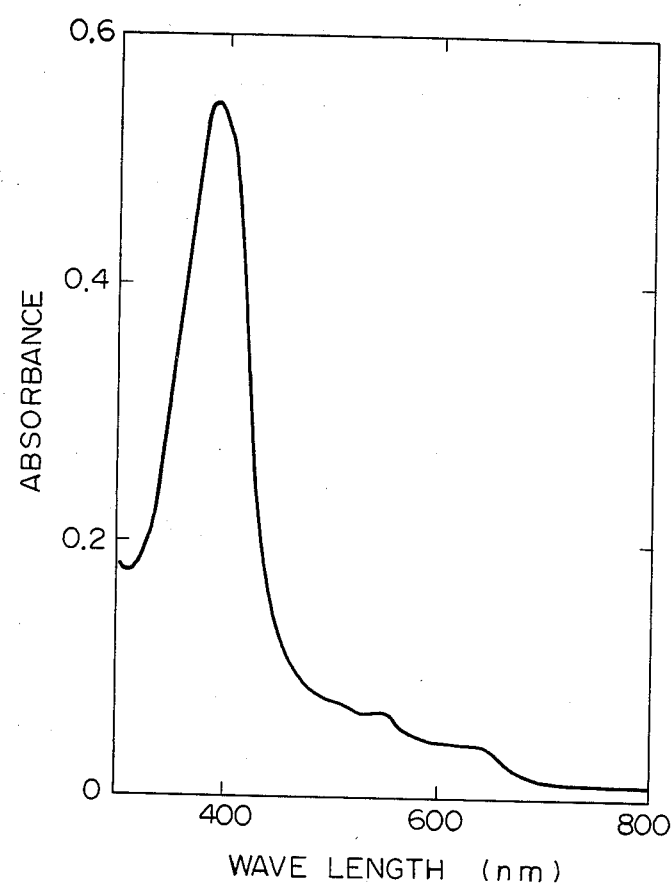
FIG. 3 shows visible to UV absorption spectrum of PEG$_2$-haemin-2 in Example 1 (2)

Haemin (Ferriprotoporhyrin chloride) (300 mg) and polyethyleneglycol monomethyl ether (average molecular weight 5,000) (5 g) were dissolved in pyridine (50 ml), molecular sieve 3A (2.5 g) was added in order to adequately remove water, and a condensation agent dicyclohexylcarbodiimide (1.25 g) was then added to complete the formation of ester bonding whereupon PEG$_2$-heamin-2 of the invention was obtained (yield 25%). FIG. 3 shows the visible to UV absorption spectrum of the purified—PEG$_2$-haemin-2, in which two carboxyl groups of the haemin have been reacted with the ether—. PEG$_2$-haemin-2.

EXAMPLE 2

Determination of peroxidase activity of the modified haemin (PEG$_2$-haemin-1)

The modified haemin obtained in Example 1 was dissolved in water (0.305 mg/ml) and 0.25 ml of the solution was added to a mixture comprised of 0.1M phosphate buffer solution (ph 7.0, 1 ml), 11.5 mM phenol (1.3 ml), 10 mM 4-aminoantipyrine (0.25 ml) and 6 mM hydrogen peroxide (0.2 ml). The mixture was allowed to react for 5 minutes at 37° C. The reaction was terminated by adding 20% sodium azide (0.2 ml) and absorption at 550 nm was measured. The peroxidase activity (U/ml) was determined from the formula:

$$\Delta A_{500} \times 0.198 \times 2 \times (\text{dilution rate})$$

The absorption value of the undiluted modified haemin was 0.539. Therefore, the peroxidase activity of the modified haemin was determined as 0.213 U/ml (0.698 U/mg).

The same reaction was conducted in an organic solvent system 1,1,1-trichloroethane/methanol (90:10) rather than in water and this resulted in a similar degree of quantitative colorination which was proportional to the hydrogen peroxide concentration.

EXAMPLE 3

Quantification of lipid peroxides by the modified haemin (PEG$_2$-haemin-1)

Figure 5:
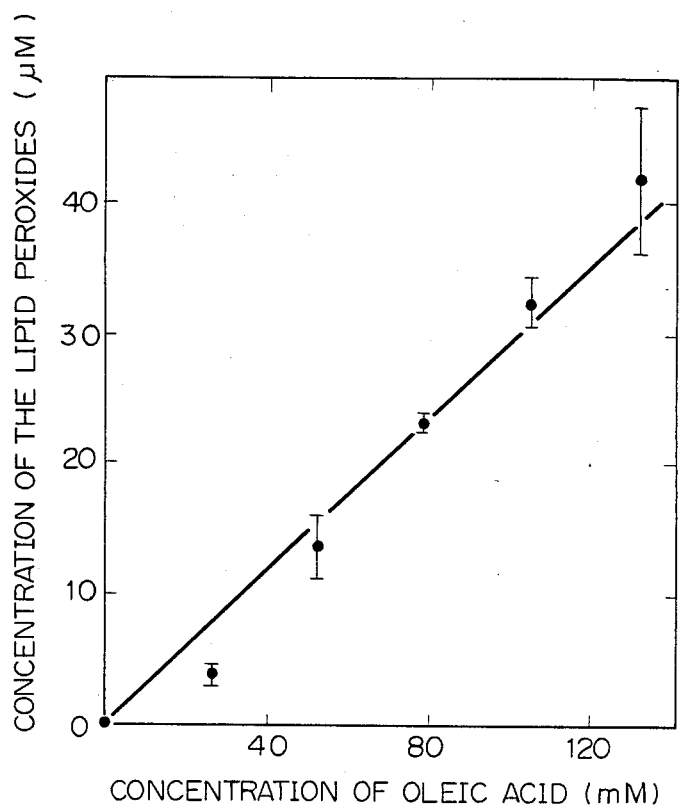
FIG. 5 is a graph showing the linear relationship between the concentration of autoxidated oleic acid in the sample solution and the concentration of lipid peroxides detected in the quantification of lipid peroxides in Example 3.

A series of solutions containing different concentrations of oleic acid which had been subjectd to autoxidation were used as samples of lipid peroxides. Each of the sample solutions (0.1 ml), 64 μM modified haemin of Example 1 (0.1 ml) and 20 mM leucocrystal violet (0.5 ml) were mixed in trichloroethane (0.5 ml) and then added to 2 ml of 1,1,1-trichloroethane containing 10% methanol. The mixture was sealed from the light and reacted at 40° C. for 25 hours under shaking. The absorption at 585 nm was measured to quantify the amount of lipid peroxides. The results are shown in FIG. 5 which shows a linear relation between the concentration of autoxidated oleic acid in the sample solution and the concentration of lipid peroxides detected.

We claim:

1. A modified haemin wherein said haemin is ferriprotoporphyrin choloride characterized by a peroxidase activity and by a solubility both in water at a neutral pH and in organic solvents, wherein one or two carboxyl groups of said haemin are coupled to the nonmethoxy end of a polyethyleneglycol monomethyl ether or an ω-amino derivative thereof through an ester bonding or an amide bonding.

2. A modified haem according to claim 1 wherein said polyalkylene glycol methyl ether is polyethylene glycol monomethyl ether of the formula:

$$CH_3O-(CH_2CH_2O)_n-H$$

wherein n is a number chosen so that the molecular weight of the ether or its derivative will be between 750 and 10,000.

3. A modified haem according to claim 2 wherein n is a number chosen so that the molecular weight of the ether or its derivative will be between 2,000 and 5,000.

* * * * *